United States Patent [19]

Queuille et al.

[11] 4,318,918
[45] Mar. 9, 1982

[54] NOVEL SALT OF 5-(BENZOYL)-THIOPHENE-2-α-METHYL-ACETIC ACID

[75] Inventors: André Queuille, Noisy-le-Sec; Gilbert Rouiller, Courbevoie, both of France

[73] Assignee: Roussel Uclaf, Paris, France

[21] Appl. No.: 705,057

[22] Filed: Jul. 14, 1976

[30] Foreign Application Priority Data

Jul. 28, 1975 [FR] France ................................ 75 23501

[51] Int. Cl.³ ..................... A61K 31/38; C07D 333/24
[52] U.S. Cl. ........................................ 424/275; 549/70
[58] Field of Search ................ 260/332.2 A; 424/275; 549/70

[56] References Cited

U.S. PATENT DOCUMENTS

| | | | |
|---|---|---|---|
| 3,466,372 | 9/1969 | Shen | 424/248 |
| 3,560,525 | 2/1971 | Kaltenbronn | 260/332.2 A |
| 3,577,549 | 5/1971 | Vack | 424/317 |
| 3,644,399 | 2/1972 | Brown | 260/326.3 |
| 3,682,964 | 8/1972 | Rousseau | 260/327 |

FOREIGN PATENT DOCUMENTS

| | | | |
|---|---|---|---|
| 1516775 | 2/1968 | France | 260/517 |
| 2068425 | of 1971 | France | 260/332.2 |
| 684682 | 1/1969 | South Africa | 260/517 |

OTHER PUBLICATIONS

"Cutting's Handbook of Pharmacology" 4th Ed. (1969), p. 261.

Primary Examiner—Alan Siegel
Attorney, Agent, or Firm—Hammond & Littell, Weissenberger and Muserlian

[57] ABSTRACT

A novel salt of 5-(benzoyl)-thiophene-2-α-methylacetic acid and tromethamine which is also known as tris (hydroxymethyl)-amino-methane of the formula

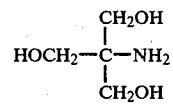

having analgesic and anti-inflammatory activity.

4 Claims, No Drawings

NOVEL SALT OF 5-(BENZOYL)-THIOPHENE-2-α-METHYL-ACETIC ACID

STATE OF THE ART

Copending, commonly assigned application Ser. No. 610,110 filed Sept. 4, 1975 describes various thiophene-acetic acids and various salts thereof including 5-(benzoyl)-thiophene-2-α-methyl-acetic acid having analgesic and anti-inflammatory activity but the said acid and its salts are not sufficiently soluble in neutral aqueous media for parenteral administration.

OBJECTS OF THE INVENTION

It is an object of the invention to provide the novel salt of tromethamine and 5-(benzoyl)-thiophene-2-α-methyl-acetic acid.

It is another object of the invention to provide novel analgesic and anti-inflammatory compositions and to provide a novel method of relieving pain and inflammation in warm-blooded animals.

These and other objects and advantages of the invention will become obvious from the following detailed description.

THE INVENTION

The novel salt of the invention is the salt of tromethamine and 5-(benzoyl)-thiophene-2-α-methyl acetic acid. The low solubility in water of 5-(benzoyl)-thiophene-2-α-methyl acetic acid made it not too suitable for administration and the salt of the present invention has good water solubility at a pH near neutral which makes it well tolerated and useful for administration by injection. The said salt is soluble in water at about 30% although the free acid is substantially not soluble in water and the said salt gives substantially neutral aqueous solution. For example, a 4% solution of the said salt has a pH of about 6.5–7.

The process of the invention for the preparation of the novel salt comprises reacting tromethamine and 5-(benzoyl)-thiophene-2-α-methyl acetic acid, preferably in an inert solvent such as water or a lower alkanol like methanol or ethanol.

The novel analgesic and anti-inflammatory compositions of the invention are comprised of an effective amount of the salt of tromethamine and 5-(benzoyl)-thiophene-2-α-methyl acetic acid and an inert pharmaceutical carrier. The compositions may be in the form of tablets, dragees, gelules, granules, suppositories, injectable solutions or suspensions, pomades, creams or gels.

The pharmaceutical carrier may be those excipients usually used and examples are talc, lactose, starch, arabic gum, magnesium stearate, mannitol, cacao butter, aqueous or non-aqueous vehicles, fatty bodies of animal or vegetable origin, paraffinic derivatives, glycols, preservatives and diverse wetting agents, dispersants and emulsifiers.

The compositions are useful for the treatment of muscular or nervous pains, rhumatismic affections, dental pain, zonas and migraines as well as a complementory treatment of feverish or infectious states.

The novel method of the invention for relieving pain and inflammation in warm-blooded animals, including humans, comprises administering to warm-blooded animals an analgesically or anti-inflammatory effective amount of the salt of tromethamine and 5-(benzoyl)-thiophene-2-α-methyl-acetic acid. The salt may be administered orally, rectally or parenterally, preferably the latter. The usual daily dose is 1 to 10 mg/kg depending on the method of administration and the condition being treated.

In the following examples there are described several preferred embodiments to illustrate the invention. However, it should be understood that the invention is not intended to be limited to the specific embodiments.

EXAMPLE 1

Tromethamine 5-(benzoyl)-thiophene-2-α-methyl-acetate 600 ml of methanol and then 400 g of 5-(benzoyl)-thiophene-2-α-methyl-acetic acid were added to a flask with constant stirring and 186 g of tromethamine were added thereto all at once. Dissolution occurred in about 20 minutes and the mixture was stirred for an hour. 3 Liters of ethyl ether were added to the mixture which was then stirred for an hour and filtered. The recovered precipitate was dried to obtain 581 g of tromethamine 5-(benzoyl)-thiophene-2-α-methyl-acetate melting at 120° C.

Analysis: $C_{18}H_{23}O_6NS$: Calculated: %C, 56.68; %H, 6.08; %N, 3.67; %S, 8.4. Found: %C, 56.7; %H, 6.1; %N, 3.5; %S, 8.4.

EXAMPLE 2

A flacon of sterile powder was prepared consisting of 100 mg of mannitol and 200 mg of 5-(benzoyl)-thiophene-2-α-methyl-acetic acid micropulverized together and the powder was dissolved just before use in a filtered solution of 121 mg of tromethamine, 36 mg of sodium chloride in sufficient distilled water for a volume of 5 ml which had been sterilized in an autoclave.

Suppositories were also prepared containing 250 mg of tromethamine 5-(benzoyl)-thiophene-2-α-methyl-acetate and sufficient excipient for a final weight of 3 g.

PHARMACOLOGICAL STUDY

Analgesic Activity

The test used was based on the fact noted by R. Koster et al [Fed. Proc., (1959), Vol. 18, page 412] wherein the intraperitoneal injection of acetic acid causes in mice characteristic repeated stretching and twisting movements which can persist for more than six hours. Analgesics prevent or suppress this syndrome which, therefore, can be considered as externalization of a diffuse abdominal pain.

A solution of 1% acetic acid in water containing 10% arabic gum was used and the dose which released the syndrome under these conditions was 0.01 ml/gm, that is 100 mg/kg of acetic acid. The test compound was administered orally one-half hour before the intraperitoneal injection of acetic acid, the mice having fasted since the day before the experiment. For each dose and for each control, which were obligatory for each test, a group of 5 animals was used. For each mouse, the stretchings were observed and counted and then added for the group of 5 during a period of 15 minutes starting immediately after the injection of acetic acid. Table I summarizes the results.

TABLE I

| Dose of product in mg/kg* | % of protection |
|---|---|
| 1.36 | 15 |

TABLE I-continued

| Dose of product in mg/kg* | % of protection |
|---|---|
| 3.41 | 53 |

*expressed in 5-(benzoyl)-thiophene-2-α-methyl acetic acid.

The $DA_{50}$ dose, the dose which reduces the number of stretchings in the treated animal as compared to the controls is about 3.4 mg/kg and the results show that the analgesic activity of 5-(benzoyl)-thiophene-2-α-methyl-acetic acid was retained by the salt.

Various modifications of the product and methods of the invention may be made without departing from the spirit or scope thereof and it is to be understood that the invention is to be limited only as defined in the appended claims.

We claim:

1. Tromethamine 5-(benzoyl)-thiophene-2-α-methyl acetate.

2. An analgesic and anti-inflammatory composition comprising an effective amount of the compound of claim 1 and an inert pharmaceutical carrier.

3. A method of relieving pain and inflammation in warm-blooded animals comprising administering to warm-blooded animals an analgesically and anti-inflammatorily effective amount of the compound of claim 1.

4. The method of claim 3 wherein the compound is administered parenterally.

* * * * *